(12) United States Patent
Spindler (10) Patent No.: US 6,174,447 B1
(45) Date of Patent: Jan. 16, 2001

(54) PROCESS AND DEVICES FOR FLUID SEPARATION OF WHOLE BLOOD AS A MIXTURE OF LIQUIDS INTO INDIVIDUAL, DIFFERENTLY-COLORED BLOOD CONSTITUENTS, IN PARTICULAR FOR SEPARATION OF CONCENTRATED THROMBOCYTES FROM BUFFY COAT

(75) Inventor: Jörg Spindler, Heidelberg (DE)

(73) Assignee: Deutsches Rotes Kreuz Blutspendendienst Baden-Wurttemberg Gemeinnützige Gesellschaft mbH, Baden-Baden (DE)

( * ) Notice: Under 35 U.S.C. 154(b), the term of this patent shall be extended for 0 days.

(21) Appl. No.: 09/029,117

(22) PCT Filed: Aug. 23, 1996

(86) PCT No.: PCT/DE96/01570

§ 371 Date: Feb. 23, 1998

§ 102(e) Date: Feb. 23, 1998

(87) PCT Pub. No.: WO97/07836

PCT Pub. Date: Mar. 6, 1997

(30) Foreign Application Priority Data

Aug. 23, 1995 (DE) .............................................. 195 30 969

(51) Int. Cl.[7] ........................... G01N 21/05; G01N 33/49
(52) U.S. Cl. .............................. 210/745; 210/85; 210/86; 210/97; 210/109; 210/143; 210/739; 356/39; 356/410
(58) Field of Search ................................ 210/85, 86, 87, 210/97, 109, 143, 252, 513, 515, 739, 745, 767, 782, 789; 222/23, 52, 96, 103, 214; 356/39, 410, 411, 414

(56) References Cited

U.S. PATENT DOCUMENTS

| | | | |
|---|---|---|---|
| 3,900,396 | 8/1975 | Lamadrid | 210/94 |
| 4,085,047 | 4/1978 | Thompson | 210/188 |
| 4,227,814 | 10/1980 | Soodak et al. | 356/410 |
| 4,810,090 | * 3/1989 | Boucher et al. | 356/39 |
| 4,976,851 | * 12/1990 | Tanokura et al. | 210/86 |
| 5,124,030 | * 6/1992 | Tanokura et al. | 210/86 |
| 5,135,646 | * 8/1992 | Tanokura et al. | 210/86 |
| 5,385,539 | * 1/1995 | Maynard | 604/4 |
| 5,734,464 | * 3/1998 | Gibbs | 356/39 |

FOREIGN PATENT DOCUMENTS

| | | |
|---|---|---|
| 3815643 | 3/1977 | (DE) . |
| 0682953 | 11/1985 | (EP) . |
| 0329786 | 8/1989 | (EP) . |
| 0611579 | 8/1994 | (EP) . |
| 2620950 | 3/1989 | (FR) . |
| 1537096 | 12/1978 | (GB) . |
| 8901796 | 3/1989 | (WO) . |

* cited by examiner

Primary Examiner—John Kim
(74) Attorney, Agent, or Firm—Horst M. Kasper (57) ABSTRACT

The invention relates to a method for fluid separation of whole blood as a mixture of liquids into individual, differently-colored blood constituents, which blood is packed in flexible containers, in particular bags, wherein the bags are connected to one another with an at least partially light-transparent connection, in particular a flexible tube, and wherein the blood constituents are forced to flow from one container through the light-transparent connection into another container, in particular for the separation of concentrated thrombocytes from buffy coat, as well as to a device for performing the method.

22 Claims, 7 Drawing Sheets

PROCESS AND DEVICES FOR FLUID SEPARATION OF WHOLE BLOOD AS A MIXTURE OF LIQUIDS INTO INDIVIDUAL, DIFFERENTLY-COLORED BLOOD CONSTITUENTS, IN PARTICULAR FOR SEPARATION OF CONCENTRATED THROMBOCYTES FROM BUFFY COAT

TECHNICAL AREA

The invention relates to a method for fluid separation of whole blood as a mixture of liquids into individual, differently-colored blood constituents, which blood is packed in flexible containers, in particular bags, wherein the bags are connected to one another with an at least partially light-transparent connection, in particular a flexible tube, and wherein the blood constituents are forced to flow from one container through the light-transparent connection into another container, in particular for the separation of concentrated thrombocytes from buffy coat, as well as to a device for performing the method.

STATE OF THE ART

There are various techniques for the separation of whole blood into its distinct constituents, in particular for the recovery of concentrated thrombocytes. At least one centrifugation for the recovery of the concentrated thrombocytes and an at least in part manual manipulation is common to all techniques. The starting product is whole blood, which is disposed in a flexible bag, wherein the flexible bag is connected air-tight and liquid-impermeable with transparent flexible tubes to further additional satellite bags, wherein the further additional satellite bags serve for receiving the separated concentrates.

After the main part of plasma and erythrocytes has been removed with a press from the bag filled with whole blood, the remaining mixture of erythrocyte cells and leucocyte cells, thrombocyte platelets as well a residue of plasma is centrifuged once again for the recovery of concentrated thrombocytes, and this so-called buffy coat is once again placed in a press in order to perform a separation of the erythrocytes and leucocytes from the now thrombocyte-rich plasma. During the pressing procedure, the operating person controls the flow of the pressed thrombocyte-rich plasma by means of a clamp at a transparent connection tube and observes as well during this procedure when the first erythrocytes and leucocytes appear in the connection tube after the transparent-yellowish plasma. If this occurs, the operating person clamps the tube, deventilates subsequently the thrombocyte bag, and welds the end of the tube.

Care is to be taken in this case that no erythrocyte cells and leucocyte cells pass into the thrombocyte bag, however also that all of the thrombocytes-platelets-plasma mixture is recovered from the original bag.

The operating person can manually control the flow rate within the tube with the clamp which surrounds the connection tube. If the flow rate is too high, there occurs a so-called siphon effect, i.e. the substantially larger erythrocyte cells and leucocyte cells are torn from the buffy-coat layer and contaminate the concentrated thrombocytes. It is difficult for the operating person to achieve a uniform flow-through rate. Based on a uniform flow and the normal bag size, this would take about 140 seconds, i.e. the operating person would have to hold the clamp for about 140 seconds at a uniform clamping pressure, which requires a high concentration of the operating person. In order to shorten this time, the operating person frequently lets the plasma-thrombocyte concentrate flow faster at the beginning and slower at the end, which indeed means a larger contamination with leucocyte cells and erythrocyte cells based on the siphon effect and leads to a non-optimum yield of the thrombocyte plasma because the buffy-coat layer was stirred up and whirled up. The operating person has to observe visually at the end of the pressing procedure when the first erythrocytes arrive in the tube. However, the operating person cannot see the first erythrocyte cells, since they are present in too small a concentration and, it is even harder that the operating person can optically perceive the practically colorless leucocyte cells. This means that the tube is clamped too early or too late depending on the disposition and attentiveness of the operating person. In case the clamping is performed too early, this means a too small thrombocyte yield up to the sorting out since the concentration of thrombocytes has to amount to $>0.5 \times 10^{11}$. Or the weight of 56 grams net of the plasma-thrombocyte yield falls short. If the tube is clamped too late, too many leucocytes and erythrocytes are present in the preparation (limit $<1.0 \times 10^8$ WBC$<2.0 \times 10^9$ RBC).

The manual recovery of thrombocyte platelets is therefore associated with a more or less large contamination of erythrocytes and leucocytes, which is the reason that the uniformity of the quality of the concentrated thrombocytes is subject to certain fluctuations. The operating person decides up to which point of discoloration, i.e. contamination, of the serum he or she allows the concentrated thrombocytes to pass. Lipaemic and strongly discolored, in particular red plasmas cannot be used in this case, since "ery" fragments and haemoglobin can for example be present in the red plasmas which cannot be centrifuged off. This means that it cannot be completely excluded that the operating person allows inadmissible concentrates of thrombocytes.

An apparatus for the separation of whole blood in a flexible, transparent bag with at least one outlet line and shut-off device is known from the German printed patent document DE 38 15 643 C1, wherein said apparatus comprises a casing with a front plate and a pressure plate, pivotable relative to the front plate, with a drive device for the pressure plate as well as a scanning device. The scanning device includes an optical detector, which can be a tube detector in the tube region and which actuates a shut-off device for one of the outlet devices when a specific component layer reaches a predetermined level in the bag. Furthermore, tube detectors as scanning devices are known from the British printed patent document GB-PS 15 37 096.

TECHNICAL TASK

It is the purpose of the invention to provide for a method and a device for the fluid separation of whole blood as a mixture of liquids into individual, differently-colored blood constituents, in particular for the separation of concentrated thrombocytes from buffy coat, wherein the separation procedure takes place automatically controlled, and wherein there occurs in particular a separation of high purity of the individual, differently-colored constituents of the whole blood.

DISCLOSURE OF THE INVENTION AND ITS ADVANTAGES

The solution of the task is characterized by a process wherein a light source, such as a transmitter diode or light-emitting diode (LED), with a more or less monochromatic radiation of the wave length in the range of either about 535 nm to 575 nm (green to red), preferably 565 nm, or from about 400 nm to 453 nm (blue), is employed as a transmitter of the photometer unit. The receiver, which is a photo resistor or photo diode or photo transistor, tuned to the wave length of the light source, detects changes in the color of the liquid and derives therefrom a signal which is transferred to a breaker unit. The connection between the containers is led through the breaker unit. The breaker unit controls the flow rate as a function of the output signal of the receiver of the photometer unit and, in particular, interrupts the flow when a predetermined limit value is reached.

The method is associated with the advantage that a fully automatically controlled separation of the whole blood or of the buffy coat into the individual, differently-colored blood constituents occurs with the method by means of a photometric differentiation and separation of the differently-colored constituents and that the individual constituents can be separated from each other and can be recovered in a high purity phase. Independent of the subjective impression of the operating person observing, a predetermined value of the color recognition of a blood constituent is again and again reproduced by the photometer unit. The preceding adjustment occurs automatically by means of the inherent coloration of the plasma. A maximum lower limit value can be determined, whereby lipaemic and haemolytic preparations are automatically excluded from the processing.

The inventor has recognized that in case of a spectral analysis of a normal serum with low erythrocyte contamination, such as of an $H_2O$ distillate with lysated erythrocytes as well as of a highly lipaemic serum with high erythrocyte contamination, all liquids in the range of from 400 nm to 453 nm (blue) and in the range of from about 535 nm to 575 nm (green to red), preferably 565 nm, show marked (hemoglobin-) maxima in the blue range and in the green range, based on which the detection therefore occurs according to the invention.

The method is suited in like manner for the detection of thrombocytes and/or leucocytes, because these can be detected based on their scattering effect. The light traversing the connection, preferably of a short wave length (blue or green-yellow to red), is dimmed and/or stopped in front of the receiver such that essentially only parallel light beams can fall onto the receiver, wherein, based on the scattering of the light at the thrombocytes and/or leucocytes, a low light yield means a high portion of thrombocytes and/or leucocytes in the liquid and vice versa. For preventing a jerky inflow of the liquid into the photometer unit, advantageously the flow rate of the liquid can be released throttled in the start phase and the flow cross-section can be released time-delayed very slowly, in particular mechanical-eccentrically by means of a mechanical cam. When the bag with buffy coat was placed into a pressure unit of the state of the art, the plasma shot up to the detector in the start-up phase because there was air in the tube. The plasma continued to flow only once the air had escaped. This could only be counteracted in that the operating person manually ventilated the tube with a clamping scissor at the beginning which, however, did not effect a slow-uniform opening.

The transmitter of the photometer unit can also be controlled in a timed way, whereby the photometer unit becomes more stable.

A device according to the invention for performing the method comprises that the transmitter of the photometer unit is a light source, such as a transmitter diode or light-emitting diode (LED) with a more or less monochromatic radiation of the wave length in the range of either about 535 nm to 575 nm (green to red), preferably 565 nm, or about 400 nm to 453 nm (blue). The receiver, which is a photoresistor or photodiode or phototransistor tuned to the wave length, is capable of detecting changes in the color of the liquid and derives a signal therefrom. Said signal is conveyed to a breaker unit. The connection between the containers is guided through the breaker unit. The breaker unit controls the flow amount as a function of the output signal of the receiver of the photometer unit and, in particular, interrupts or stops the flow upon reaching a predetermined limit value.

The device is more sensitive by a multiple than the human eye; it can recognize thrombocytes and/or leucocytes as well as already the smallest red erythrocyte amounts, which means that during the pressing procedure of the buffy coat erythrocytes or leucocytes cannot pass any longer into the thrombocyte bag or, respectively, into the concentrated thrombocytes, because the device clamps the connection tube beforehand. Furthermore, a uniform flow rate is maintained. The whirling-up and mixing of the thrombocyte-rich plasma in the buffy-coat layer with the leucocyte-erythrocyte layer does not occur (siphon effect), wherefore no contamination of the concentrated thrombocytes occurs. A maximum thrombocyte-rich plasma yield can thereby be achieved. In addition, the device does not proceed with the separation procedure of the buffy coat in case of a certain plasma contamination; there occurs an immediate interruption of the flow by means of the breaker unit. Furthermore, practically all pressure units available in the market can be retrofitted with the device.

The flow-limiting unit, for example a wedge, serves in an advantageous way also for adapting the device to the different pressing pressures of the different commercially available pressure units for pressing such blood bags.

A further advantage of the device resides in that the leucocyte concentration and erythrocyte concentration in the concentrated thrombocytes is markedly lower than is the case in the state of the art or, respectively, in the manual packing method. This means a medical improvement of the concentrated thrombocytes, namely a decrease of the allo-immunization rate which leads to a reduction in the need of filtered or, respectively, single-donor preparations. In addition, a more uniform filling weight of the thrombocyte plasma is accomplished and a concentration of thrombocytes $>0.5 \times 10^{11}$ is also assured in the concentrated thrombocytes which concentrated thrombocytes were recovered with the device.

PATHS TO THE EXECUTION OF THE INVENTION

Figure 1:
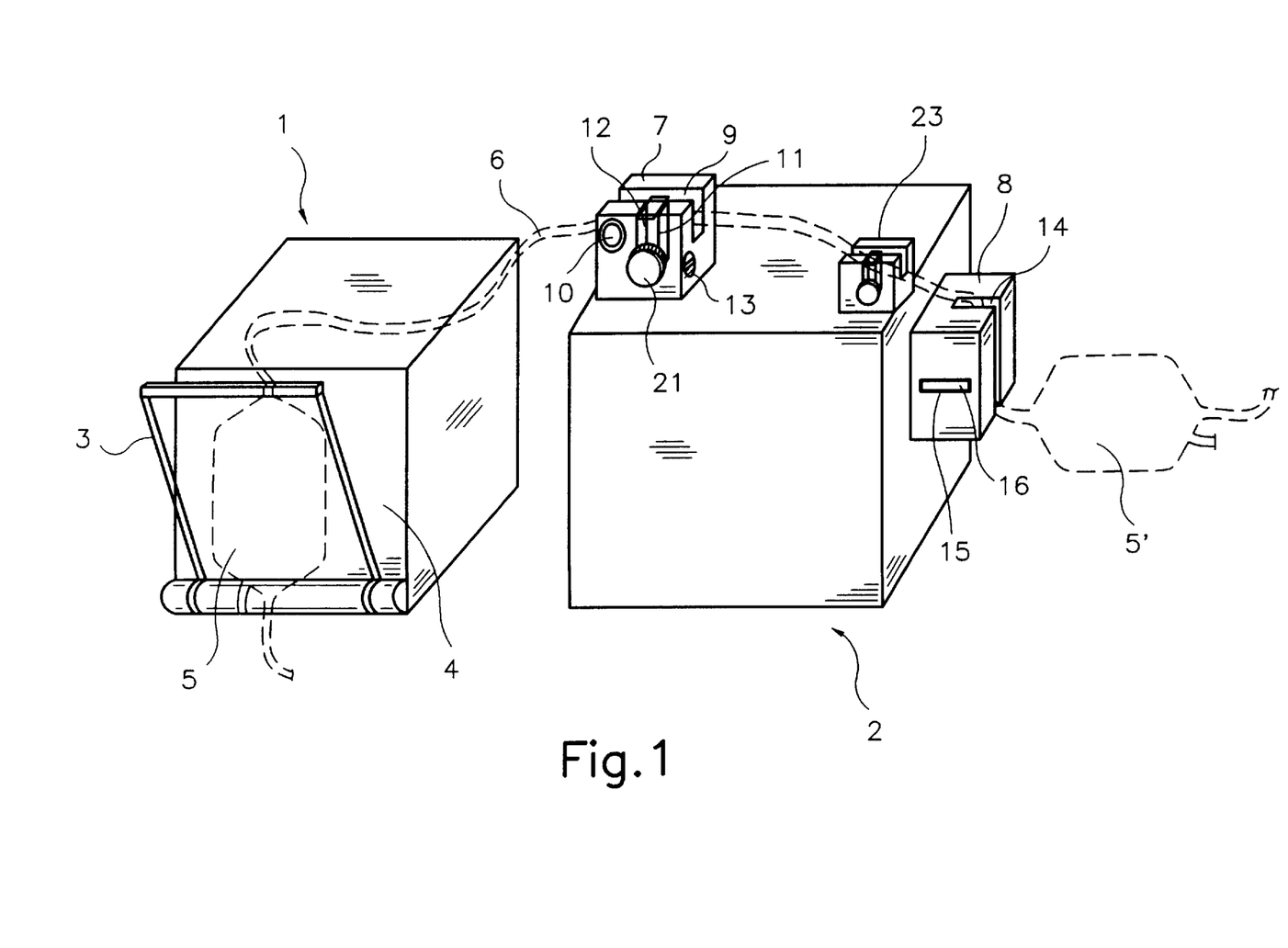
FIG. 1 a separation station including a pressure unit, a measuring device for differentiating the plasma-thrombocyte concentrate from the erythrocyte cells and leucocyte cells, and a breaker unit for interrupting the flow between two bags.

FIG. 1 shows a device for the automatically controlled separation of whole blood into the individual blood constituents or, respectively, for the recovery of a thrombocyte-rich plasma, concentrated thrombocytes, from the buffy coat. A conventional pressure unit 1, which can be a pressure unit for whole blood or for buffy coat, comprises in a known manner a pressure plate 3, pivotably disposed at the front side 4, wherein the pressure plate is preferably transparent. A bag 5, filled with whole blood or buffy coat, is placed between the pressure plate 3 and the front side 4. The bag 5 is connected with at least one light-permeable flexible tube 6 to at least one satellite bag 5' for receiving the various constituents of the blood, recovered during the separation, in this case for recovering the concentrate of thrombocytes. The tube 6 is guided over a clamping block 7, wherein the clamping block 7 is mounted on a measuring device 2, and subsequently the tube 6 is guided through a breaker unit 8.

The clamping block 7 is preferably detachably mounted on the measuring device 2 so that the distance of the clamping block 7 from the pressure unit 1, and thus the tube length of the tube 6 from the pressure unit 1 to the clamping block 7 can be varied by the user. Therefore, the clamping block 7 can preferably represent a separate unit without a support, which is only connected to its necessary feed lines including the tube 6. In a similar manner, the clamping block can in each case be mounted later to the different pressure units. The clamping block, which is shown in FIGS. 4 to 7, is preferably formed parallelepipedally and exhibits a longitudinal channel 9 for the insertion of the tube 6 according to FIG. 1. A cross channel 11 is disposed crosswise to the longitudinal channel 9 within the clamping block. A wedge 12 is shiftably disposed in the cross channel 11 as flow-limiting unit. The wedge 12 can be locked and arrested in a simple embodiment by means of a setscrew 13 in a desired predetermined position within the cross channel 11. The adjustment of the wedge 12 occurs manually, preferably with an adjusting screw 21, such as a micrometer screw, which engages in a suitable way at the wedge 12 in order to displace same in a transverse direction upon rotation. The flexible tube 6, inserted and placed into the longitudinal channel 9, can be clamped more or less with the wedge 12 in order to change the flow through the tube 6.

Figure 8:
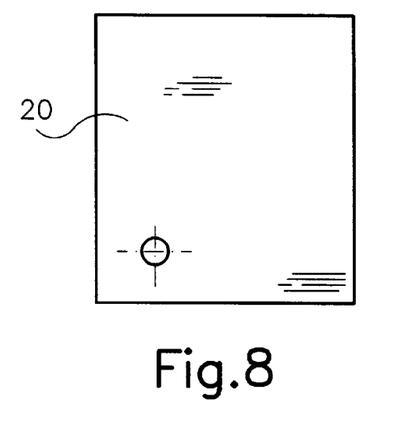
FIG. 8 a cover plate for covering the clamping block.

The clamping block 7 houses at the same time a photometer unit. The photometer unit includes a transmitter 10, which transmitter includes a light source, in particular a light-emitting diode, and a receiver 18 which is a photoresistor or a photodiode or a phototransistor. The transmitter 10 and the receiver 18 are preferably disposed in each case in a borehole crosswise to the longitudinal channel 9 of the clamping block and opposite to each other in flow direction of the liquid in front of the wedge 12, which can best be seen from FIG. 4. The light source 10 generates a preferably monochromatic radiation with a wave length of preferably 565 nm (green). The receiver 18 exhibits its highest sensitivity or, respectively, the largest output signal in case of the irradiation of the red erythrocytes preferably in the green spectrum. The value of the thrombocyte-leucocyte-erythrocyte recognition can in this case be preselected within wide ranges. The flow rate of the blood through the clamping block 7 as well as the adaptation to different pressure devices can be set with the wedge 12. The quality of the concentrated thrombocytes can still be changed or, respectively, controlled with the corresponding tube length in front of the head of the photometer. The clamping block 7 is covered with a cover platelet, which is shown in FIG. 8, in order to exclude external light influences to the largest extent possible.

In addition, a schematically represented breaker unit 8 is disposed at the measuring device 2. The breaker unit 8 also exhibits a channel 14, wherein the tube 6 is guided through the channel 14. A cross channel 15 is suitably disposed relative to this channel 14. An electromagnet with a movable part 16 is shiftably disposed in the cross channel 15, wherein the part 16 is conically pointed in the front in its squeezing region, and wherein the part 16 is moved with an electrical exciter coil (not shown) within the breaker block (8).

The Mode of Operation of the Device is as Follows:

The buffy coat is placed between the pressure plate 3 and the front casing wall 4 of the pressure unit. Simultaneously, the connection tube 6 is placed and inserted into the longitudinal channel 9 of the clamping block 7. The other end of the tube 6 with the satellite bag 5', attached to the other end of the tube 6, is inserted into the breaker unit 8. The plasma is now pressed with the pressure plate 3 out of the bag 5 and transferred into the satellite bag 5'. As soon as the first thrombocytes and or leucocytes or, respectively, erythrocytes in the tube 6 pass the head of the photometer, i.e. as soon as the set value of the recognition within the photometer is reached, the receiver 18 emits a start pulse, and the movable part 16 of the electromagnet responds based on the start pulse and quickly squeezes the tube 6 shut and thereby the breaker unit 8 interrupts the flow into the satellite bag 5'. Subsequently, the tube 6 is severed, the thrombocyte bag 5' is deventilated, and the end of the tube at the thrombocyte bag 5' is welded.

Figure 9A:
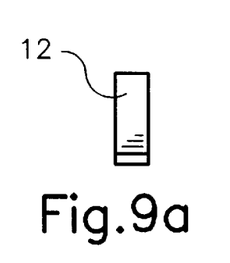
FIGS. 9a, b, c three different views of the wedge within the clamping block for limiting the flow.
Figure 9B:
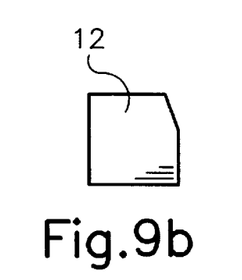
Figure 9C:
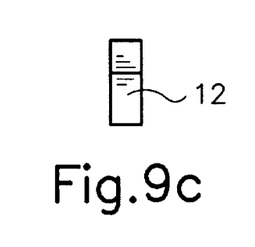

The cooperation between the wedge 12 and the photometer within the clamping block is of decisive importance because contamination of the concentrated thrombocytes by the buffy coat layer can only be effectively prevented based on the setting of a uniform, adapted flow rate by means of the wedge. The reason for this is that the substantially larger leucocyte cells and erythrocyte cells are retained, held back, and banked up at the narrowing of the clamping block 7, however the much smaller thrombocyte platelets can easily pass through the narrowing according to the dam principle. If the flow rate is chosen too high, the larger leucocyte cells and erythrocyte cells are now suddenly entrained. The wedge 12 is shown in different embodiments in FIGS. 9a, b, and c.

It is advantageous to control the transmitter 10 in a pulsed and timed way because a longer service life and a better stabilization of the receiver 18 can thereby be achieved. The transmitter or, respectively, the transmitter diode, can have its own power supply. Two electrical threshold values are given upon the setting of the receiver 18 or, respectively, the receiver diode, wherein a switching process occurs at said threshold values. The receiver 18 can also exhibit its own power supply. As soon as the head of the photometer or, respectively, the receiver 19 has given a closing signal to the electromagnet 16, a switching can only be triggered again, when a specific threshold value has been reached.

In addition, a light diode can be employed which emits spectrally or, respectively, monochromatically both a green and/or up to red and/or blue radiation. The receiver or, respectively, the receiver diode must be able to detect the different wave lengths. In this way, it can also be determined, in addition to the red erythrocytes, whether additional dark or differently-colored constituents, which are not red, are present within the mixture. In this case there can also be triggered an interrupting of the process of the flow. After triggering the electromagnet of the breaker unit 8, it is imperative that the electromagnet remain attracted until the operating person releases it.

The photometer unit not only detects erythrocytes, which tend colorwise toward the yellow-red region and are preferably detected by means of light of the wave length 565 nm, but also thrombocytes and leucocytes, which are more or less white and cannot be recognized with the naked eye based on their smallness in the plasma. It is particularly important for the manufacture of concentrated thrombocytes of high purity to detect these. There occurs a scattering effect by the small thrombocytes and also by the leucocytes based on the short-wave lights (blue or green to red), wherein this scattering effect can be evaluated in that an adjustable diaphragm is disposed in front of the receiver of the photometer unit, and wherein this diaphragm is selected so small that practically only parallel light arrives at the receiver. The more thrombocytes and/or leucocytes that are present in the liquid, the less light arrives at the receiver because the scattered light cannot pass the diaphragm. If no thrombocytes and/or leucocytes are present, there occurs little scattering such that a high light yield at the receiver of the photometer is associated therewith, wherein an even larger scattering occurs in case of leucocytes alone.

As recited above, the flow rate at the start phase can be throttled and the flow cross-section can be released time-delayed very slowly, in particular mechanicaleccentrically by means of a mechanical eccentric cam, in order to prevent a sudden flow-in of the liquid into the photometer unit. For this purpose, the tube 6 can be guided through a separate, mechanical eccentric cam 23 for an opening, which eccentric cam 23 is disposed in the immediate proximity of the breaker unit 8. Or the movable part 16 of the electromagnet of the breaker unit 8 can additionally act as eccentric cam 23 for the opening and be integrated into the breaker unit 8.

Figures 2, 3:
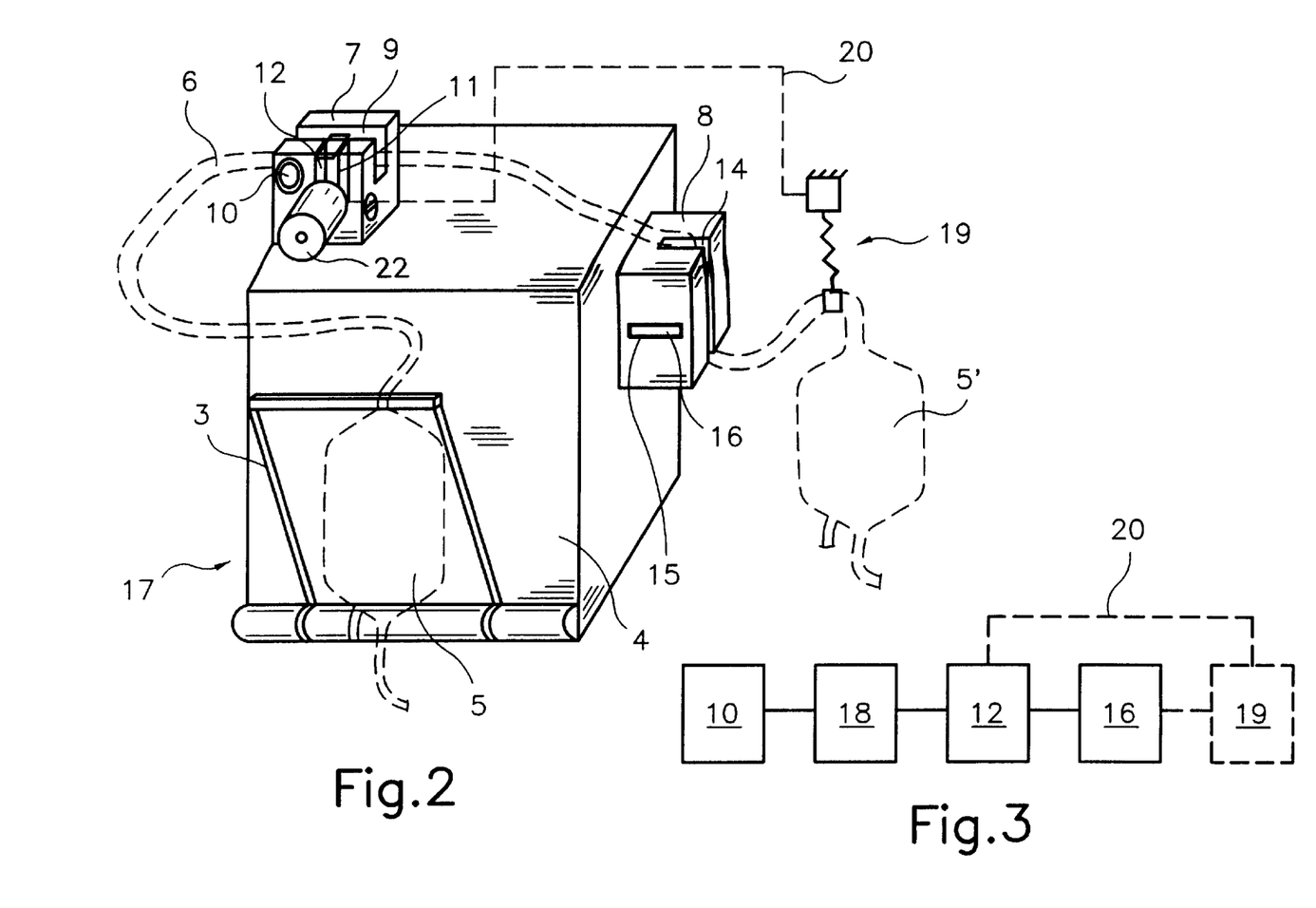
FIG. 2 a compact apparatus with a scale for the bag for the recovery of the plasma-thrombocyte concentrate for the control of the flow amount within the photometer unit.
FIG. 3 a block diagram of the essential components of the device.
Figure 4:
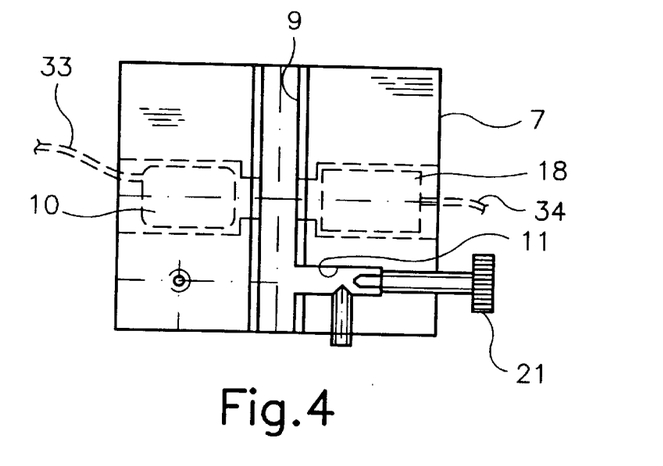
FIG. 4 a top view onto the clamping block of FIG. 1.
Figure 5:
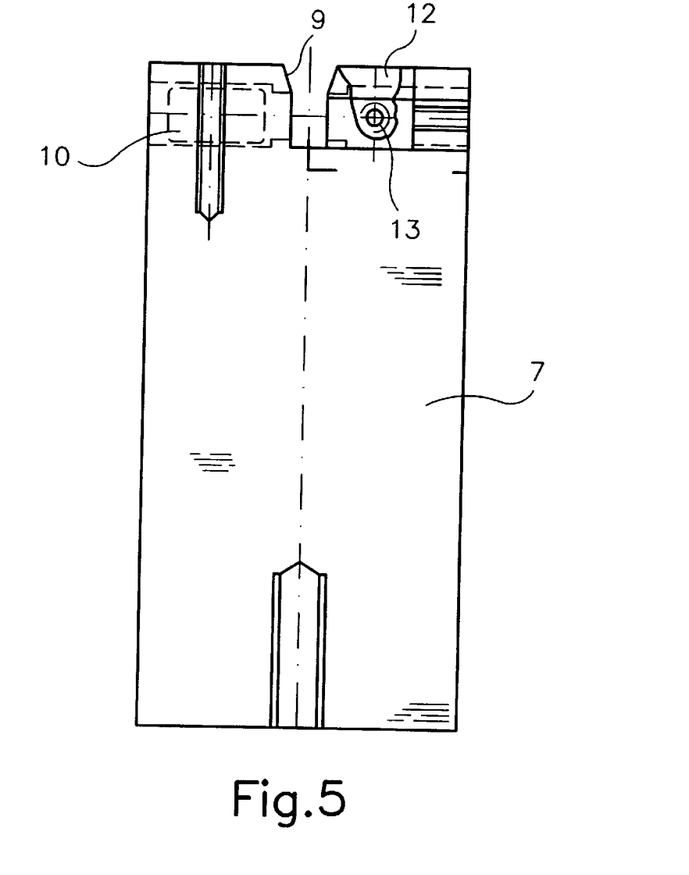
FIG. 5 a side view of the clamping block according to FIG. 4.
Figure 6:
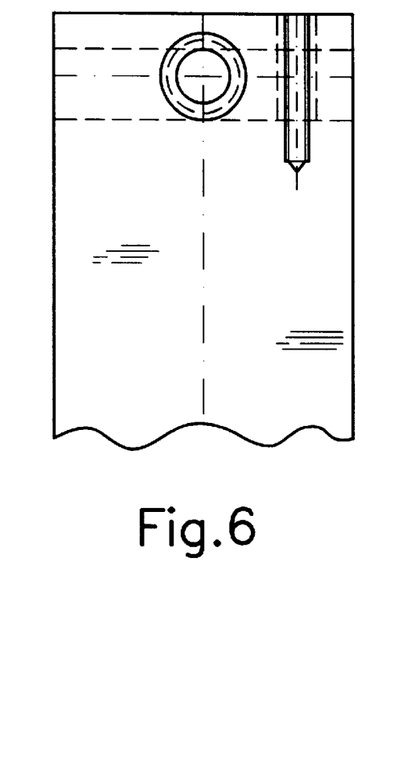
FIG. 6 a view of FIG. 5 rotated by 90 degrees.
Figure 7:
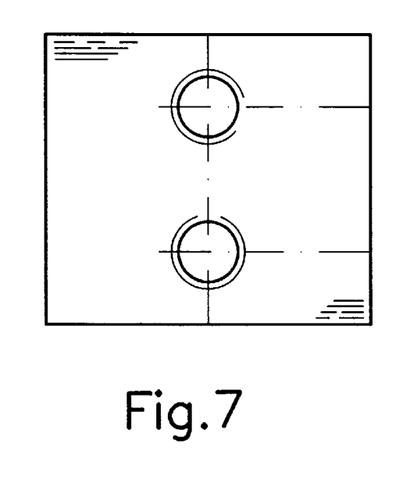
FIG. 7 a view of the underside of the clamping block.

FIG. 2 shows a further example of a separator-compact apparatus 17, wherein the same elements as in FIG. 1 are designated with the same reference numerals.

As distinguished from FIG. 1, the flow rate of the concentrated thrombocytes into the satellite bag 5' can in this case be controlled with the tube 6. For this purpose, the satellite bag 5' hangs on a scale 19, which generates continuously an electrical set signal dependent on the weight of the bag 5', wherein the set signal is given through a line 20 to an electromotor 22 or step motor within the clamping block 7. The electromotor shifts the wedge 12 by motor action within the cross channel 11 in a transverse direction such that the tube is more or less squeezed and the flow resistance of the liquid through the tube 6 and thus the flow can therewith be controlled. The flow rate is determined through the weight gain of the bag 5' per minute and is correspondingly controlled in dependence of the threshold values of the photometer. In addition, the wedge can act as an eccentric cam for an opening and can be slowly opened through the electromotor 22.

FIG. 3 shows a block diagram of the sequentially essential components of the device comprising a transmitter 10, a receiver 18, and a wedge 12, wherein the electromagnet 16 is disposed following the wedge 12. The dash-lined weighing apparatus acts through the line 20 back on the displacement device for shifting the wedge 12, which can be driven by means of an electromotor 22. The transmitter of the photometer unit 10 can be a transmitter for radiating green and/or red and/or blue radiation. In this case, the receiver 18 has a corresponding band width and is capable to differentiate between the different wave lengths. The transmitter of the photometer unit can be a white-light lamp with a filter for generating a green and/or red and/or blue monochromatic radiation. In this case, the receiver is also formed correspondingly wide-banded. For the slow opening of the flow cross-section of the tube, an eccentric cam can also act on the wedge 12 of the flow limiting unit 7, whereby the wedge is capable of releasing the flow cross-section very slowly. Or the step motor can shift the wedge in an eccentrical non-uniform way. Until the plasma arrives, the clamping is thereby reinforced, afterwards the cross-section of the flow limiting unit 7 is slowly released.

Figure 10A:
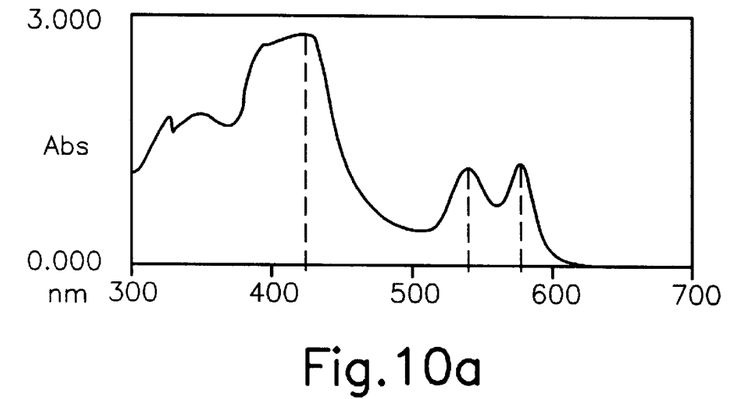
FIGS. 10a, b, c spectral analysis of $H_2O$ distillate with lysated erythrocytes, strongly lipaemic serum with high erythrocyte contamination, normal serum with low erythrocyte contamination.
Figure 10B:
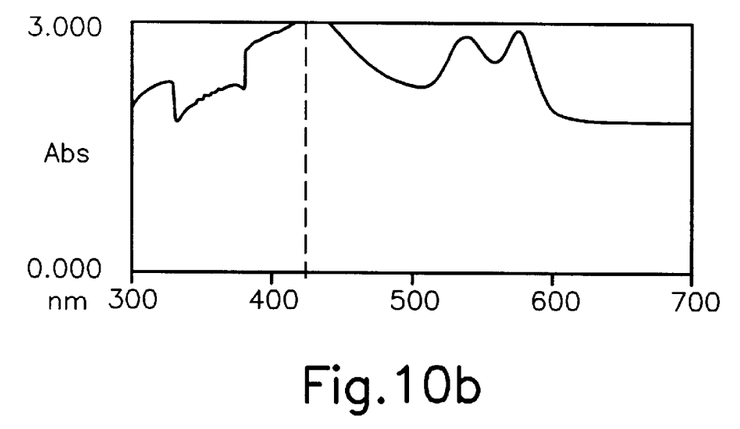
Figure 10C:
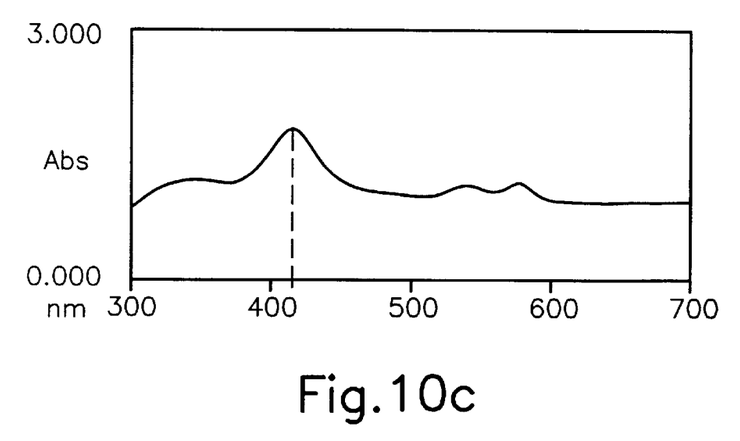

FIGS. 10*a, b, c* show three spectral analyses, namely a) of $H_2O$ distillate with lysated erythrocytes, b) of a highly lipaemic serum with high erythrocyte contamination, as well as c) of normal serum with low erythrocyte contamination. It can be recognized that in all three cases more or less marked (hemoglobin-)absorption-maxima are present in the range of either from about 535 nm to 575 nm (green, yellow, up to red), preferably 565 nm, as well as from about 400 nm to 453 nm (blue), which can be detected.

Figure 11:
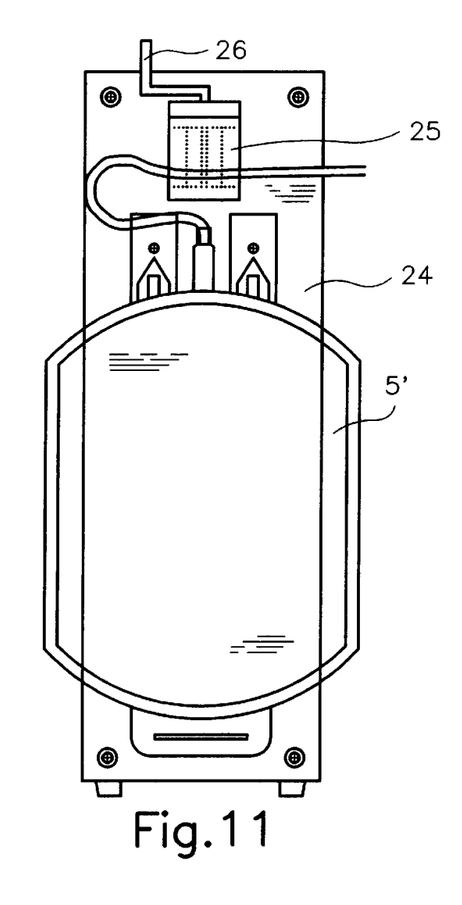
FIG. 11 the front view of a further pressure unit with an eccentric cam disposed in an opening.
Figure 12:
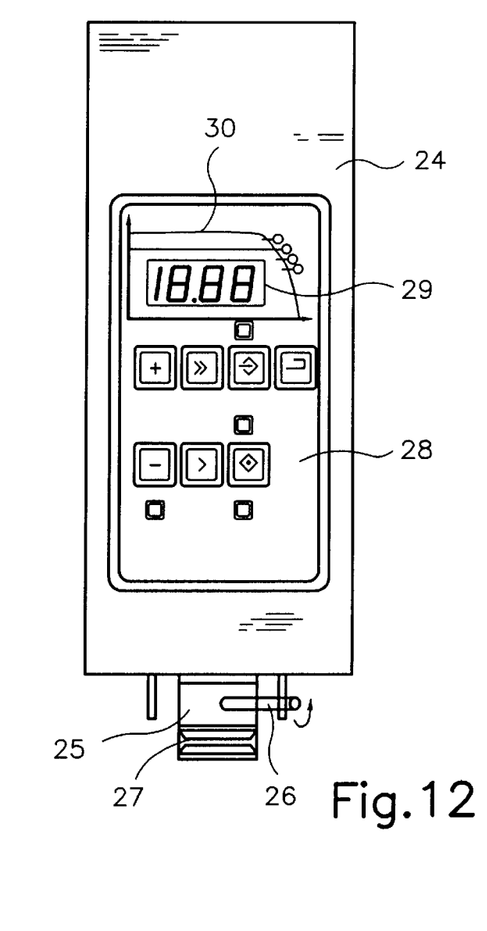
FIG. 12 the top view onto the pressure unit of FIG. 11.

FIGS. 11 and 12 show a further measuring device 24 with a bag 5', wherein a breaker unit 25 is disposed above the bag 5'. The tube of the bag passes through the breaker unit 25, as is the case in FIGS. 1 or 2, wherein its movable part of the electromagnet is in addition formed as an eccentric cam for the opening (the separate photometer unit is not shown). The movable part of the magnet can be manually opened and closed with a small crank handle 26. The movable part with the movable clamping jaws 27 can be recognized in the top view of FIG. 12 onto the measuring device 24. The motion of the movable part with the movable clamping jaws occurs very slowly during the opening procedure with the crank handle 26 and closes quickly upon actuation by the electromagnet. The measuring device 24 includes further a display 28 with a keyboard for entering an individual setting, and a voltage display, by means of which the instant coloration of the fluid including thrombocytes and leucocytes in the measurement unit (volt) is indicated.

Figure 13:
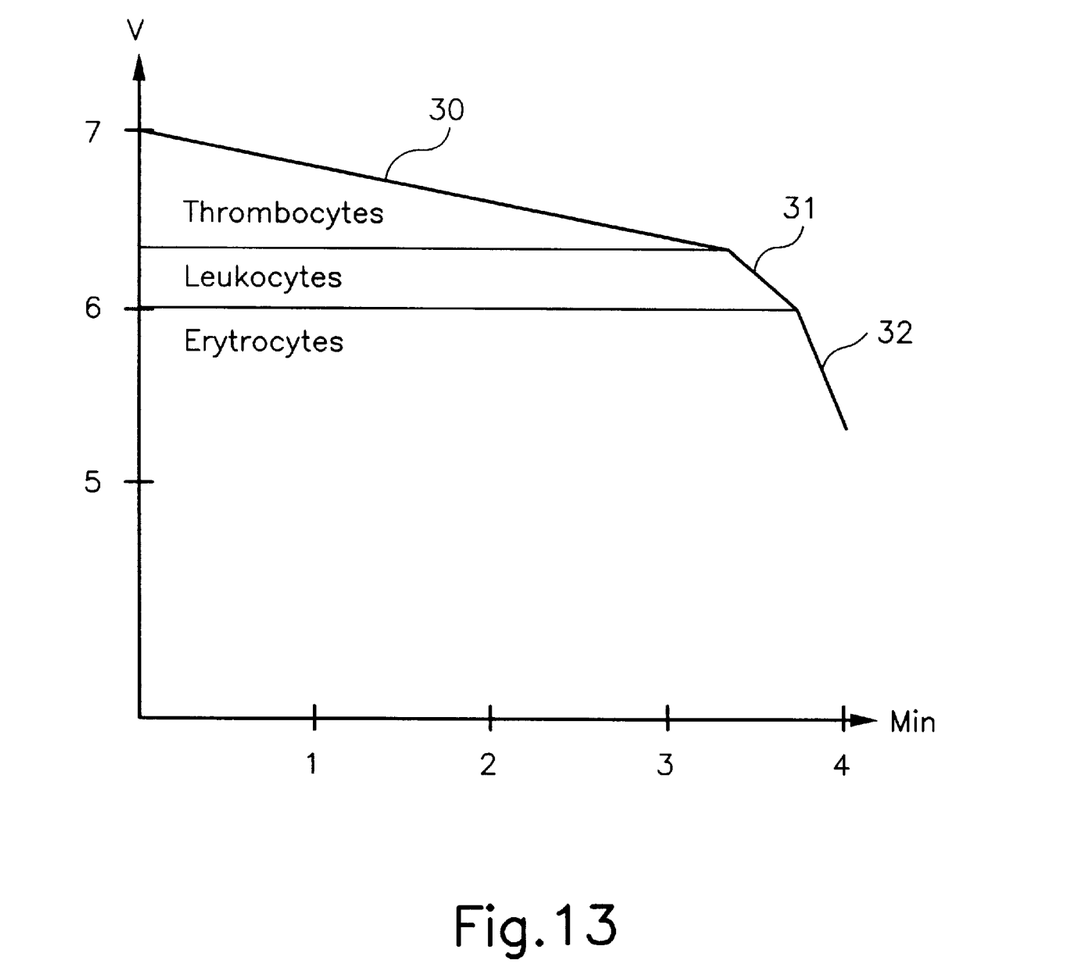
FIG. 13 a voltage time diagram of concentrated thrombocytes.

FIG. 13 shows a typical diagram voltage versus time of concentrated thrombocytes. The voltage drops only a little linearly during the withdrawing of the thrombocytes, and there results the branch 30. As soon as the drop curve reaches the grade of the branch 31, which is the case as a result of the withdrawing of leucocytes, a clamping-off takes place. When the erythrocytes are drawn off, there occurs again a massive voltage drop corresponding to branch 32. It becomes clear from this diagram that it is important to detect thrombocytes and leucocytes for a recovery of concentrated thrombocytes of highest purity.

In order to receive very pure concentrated thrombocytes, a small voltage value, for example 0.75 V, has to be deducted from the individual inherent coloration of the plasma, which occurs automatically in a memory storage of the device. Once the value is reached, the electromagnet 16 clamps off the breaker unit 8, the electromagnet 16 only opens when a specific value is reached. Based on the individual withdrawal of the inherent coloration of the plasma, it is achieved that at least 90% of the plasma is pressed off up to a residual amount, which remains in the bag of the pressure unit 1. In order to recover also the residual amount, one can start the process again, however, with a lower voltage withdrawal value. For this reason, the instant voltage value less a subsequent lower draw-off value of for example 0.3 V is stored. The same effect can be achieved with the setting of a delta V, which corresponds to the slope or grade of the branch 31. As soon as the transition from voltage branch 30 to the voltage branch 31 occurs, a very targeted clamping can take place, which corresponds to an even better optimization.

It is possible to provide two sensor systems for this purpose, preferably with a measuring bridge for the balancing, wherein the sensor systems are either disposed within the clamping block 7, spaced from one another by about 1 cm, or wherein one sensor system is disposed in the clamping block 7 and the other in the breaker unit 8. A differential measurement (delta V) can thereby be achieved and a precise clamping can be made possible.

Industrial Application:

The method and the device are suited to separate whole blood or buffy coat, which is disposed following one or, respectively, two centrifugations in a bag with satellite bags, into its differently-colored constituents, wherein said bags are connected to each other by means of transparent tubes, in particular for recovering concentrated thrombocytes of high purity. The pressing-off procedure of the bag or, respectively, of the buffy coat is controlled by means of a device according to the differently-colored constituents of the blood, wherein the constituents thrombocyte-rich plasma, enriched with thrombocytes on the one hand, and residual erythrocytes and leucocytes on the other hand, are recovered during the treatment of the buffy coat.

List of the Reference Numerals:

| | |
|---|---|
| 1 | Pressure unit |
| 2, 24 | Measuring device |
| 3, 27 | Pressure plate |
| 4 | Casing wall |
| 5, 5' | Bag |
| 6 | Tube |
| 7 | Clamping block |
| 8, 25 | Breaker unit |
| 9, 14 | Channels |
| 10 | Transmitter or, respectively, light diode |
| 11, 15 | Cross channels |
| 12 | Wedge |
| 13 | Setscrew |
| 14 | Electromagnet |
| 17 | Separator compact apparatus |
| 18 | Receiver |
| 19 | Scale |
| 20 | Cover platelets |
| 21 | Adjusting screw |
| 22 | Electromotor |
| 23 | Eccentric cam for an opening |
| 26 | Crank handle |
| 27 | Clamping jaw |
| 28 | Display |
| 29 | Voltage display |
| 30, 31, 32 | Curve branches |

What is claimed is:

1. A method for fluid separation of components of blood into individual, differently-colored blood constituents comprising the following steps:

placing components of blood as a mixture of liquids in a first flexible container (5);

connecting the first flexible container (5) to a second flexible container (5') by an at least in part light-transparent connection (6);

forcing blood constituents to flow from the first flexible container (5) through the light-transparent connection (6) into the second flexible container for a separation of concentrated thrombocytes from buffy coat;

employing an optical-electrical photometer unit (10, 18), disposed in a region of the light-transparent connection (6), wherein a transmitter (10) and a receiver (18) for electromagnetic waves are disposed in the optical-electrical photometer unit, and wherein the blood constituents within the light-transparent connection past the optical-electrical photometer unit, wherein a light source is employed as the transmitter (10) of the optical-electrical photometer unit (10, 18) having a substantially monochromatic radiation of a wave length in a range either of from about 535 nm to 575 nm, or from about 400 nm to 453 nm;

dimming the light source in front of the receiver for allowing essentially only parallel light beams fall onto the receiver, wherein the receiver (18) is at least one of a photo resistor and a photo diode (18) and a photo transistor tuned to the wave length;

guiding the light-transparent connection (6) through a breaker unit (16);

automatically deducting a signal, corresponding to inherent coloration of a plasma, from an output signal of the receiver (18) for forming a difference signal, and wherein the difference signal serves for control of the breaker unit, and wherein the breaker unit controls flow of the blood constituents and interrupts and stops the flow upon reaching of a predetermined limit value of a value of the difference signal.

2. The method according to claim 1, wherein a maximum value for the value of the difference signal is predetermined for the inherent coloration of the plasma and processing of a blood preparation is excluded when the maximum value is exceeded, whereby lipemic and hemolytic preparations are automatically excluded from the processing.

3. The method according to claim 1, wherein to increase purity of the blood constituents, a further signal of a low value relative to the signal value corresponding to the inherent coloration of the plasma is deducted from the output signal of the receiver in addition to the signal, corresponding to the inherent coloration of the plasma.

4. A method for fluid separation of components of blood as a mixture of liquids into individual, differently-colored blood constituents comprising following steps:

placing components of blood as a mixture of liquids in a first flexible container (5);

connecting the first flexible container (5) to a second flexible container (5') by an at least in part light-transparent connection (6);

placing the light-transparent connection (6) into a breaker unit (16);

forcing blood constituents to flow from the first flexible container (5) through the light-transparent connection (6) into the second flexible container for a separation of concentrated thrombocytes from buffy coat;

employing two optical-electrical photometer units (10, 18), disposed in a region of the light-transparent connection (6), wherein a transmitter (10) and receivers (18) for electromagnetic waves are disposed in the optical-electrical photometer units, and wherein the blood constituents within the light-transparent connection past the optical-electrical photometer unit, wherein a light source serves as transmitter (10) of the photometer unit (10, 18) having a substantially monochromatic radiation of a wave length in a range either of from about 535 nm to 575 nm, or from about 400 nm to 453 nm;

dimming a light in a front of the receivers for allowing essentially only parallel light beams fall onto the receivers, and wherein the receivers (18) are at least one of a photoresistor and a photodiode (18) and a photo transistor tuned to the wave length;

deriving a signal from a difference delta V of output signals of the receivers of the photometer units, wherein the signal electronically controls flow of the blood constituents.

5. The method according to claim 1, wherein flow amount of the blood constituents is throttled in a start phase and a flow cross-section of the light-transparent connection is released time-delayed very slowly in a mechanical-eccentrical way, until after the escape of air for preventing a jerky inflow of the blood constituents into the photometer unit (10, 18).

6. The method according to claim 1, wherein
the transmitter (10) of the photometer unit is controlled in a pulsed way.

7. The method according to claim 1, wherein based on a scattering of the light at thrombocytes and/or leucocytes, a low amount of unscattered light indicates a high portion of the thrombocytes and/or leucocytes in the blood constituents.

8. A device for fluid separation of components of blood as a mixture of liquids into individual, differently-colored blood constituents comprising:

a first flexible container (5);

a second flexible container (5') connected to the first flexible container (5) by an at least in part light-transparent connection (6);

a breaker unit (16) surrounding the light-transparent connection (6) and controlling a flow of the blood constituents and disposed between the first flexible container (5) and the second flexible container (5');

an optical-electrical photometer unit (10, 18), disposed in a region of the light-transparent connection (6) and having a transmitter (10) and a receiver (18) for electromagnetic waves, wherein the transmitter (10) of the optical-electrical photometer unit is a light source with a substantially monochromatic radiation of a wave length in a range either of from about 535 nm to 575 nm, or from about 400 nm to 453 nm, and wherein the receiver (18) is one of a photo resistor and a photo diode (18) and a photo transistor tuned to the wave length;

a diaphragm disposed in a front of the receiver (18) for allowing only parallel light beams fall on the receiver (18), and wherein a signal, corresponding to an inherent coloration of plasma, is automatically deducted from an output signal of the receiver (18) for forming a difference signal, and wherein the difference signal is fed to the breaker unit (16), wherein the breaker unit (16) controls the flow of the blood constitutes as a function of the difference signal and interrupts the flow upon reaching a predetermined limit value for the value of the difference signal.

9. A device for fluid separation of components of blood as a mixture of liquids into individual, differently-colored blood constituents comprising:

a first flexible container (5);

a second flexible container (5') connected to the first flexible container (5) by an at least in part light-transparent connection (6);

a breaker unit (16) surrounding the light-transparent connection (6) and controlling a flow of the blood constituents and disposed between the first flexible container (5) and the second flexible container (5');

two optical-electrical photometer units (10, 18), disposed in a region of the light-transparent connection (6) and having transmitters (10) and receivers (18) for electromagnetic waves, wherein the transmitters (10) of the optical-electrical photometer units are light sources with a substantially monochromatic radiation of a wave length in a range either of from about 535 nm to 575 nm, or from about 400 nm to 453 nm;

diaphragms disposed in front of the receivers of the photometer units for allowing only parallel light beams fall onto the receivers (18), and wherein the receivers (18) are one of a photo resistor and a photo diode (18) and a phototransistor, wherein a signal is derived from the difference delta V of output signals of the receivers of the photometer units, wherein said signal is fed to the breaker unit (16), wherein the breaker unit controls the flow of the blood constitutes as a function of the difference signal and interrupts the flow upon reaching a predetermined limit value for the value of the difference signal.

10. The device according to claim 9, wherein
the photometer units (10, 18) are provided with a measuring bridge or a resistance bridge for balancing.

11. The device according to claim 8, further comprising a clamping block, wherein the photometer unit is integrated into the clamping block, wherein the light-transparent connection (6) between the first flexible container (5) and the second flexible container (5') is guided within the clamping block, wherein the transmitter (10) and the receiver (18) are disposed neighboring to the light-transparent connection (6); and a flow-limiting unit provided for limiting and controlling the flow of the blood constituents and disposed neighboring after the photometer unit, and wherein the flow-limiting unit forms a settable flow resistance for the blood constituents within the connection (6).

12. The device according to claim 9, wherein
the breaker unit exhibits a movably supported electromagnet (16) for clamping the light-transparent connection, wherein the electromagnet (16) is electronically controllable by the receiver (18) of the photometer unit based on the signal derived from the difference delta V.

13. The device according to claim 8, wherein
the receiver (18) has a corresponding band width in the green-red range and blue range, respectively, amounting to about 15% of a wave length range, for differentiating between different wave lengths.

14. The device according to claim 8, wherein
the transmitter of the photometer unit is a white-light lamp with a filter for generating a green and/or red and/or blue monochromatic radiation.

15. The device according to claim 11, wherein
the clamping block (7) exhibits a longitudinal channel (9), wherein the light-transparent connection (6) is guided within the longitudinal channel (9), wherein a cross channel (11) joins into the longitudinal channel (9), and wherein the flow-limiting unit (12) is disposed within the cross channel (11).

16. The device according to claim 15, wherein
the flow-limiting unit is a wedge (12), wherein the wedge (12) is shiftably disposed within the cross channel (11) for a lesser or stronger squeezing the light-transparent connection (6) depending on a position of the wedge.

17. The device according to claim 16, wherein
the wedge (12) is shiftable manually by means of a micrometer screw (21), or by motor action by means of an electromotor, and by a displacement device, connected to the wedge and the electromotor.

18. The device according to claim 17, wherein
the second flexible container (5'), into which a part of the blood constituents is pressed from the first flexible container (5), is hung at a weighing device (19) for a continuous determination of a filling weight of the second flexible container (5').

19. The device according to claim 18, wherein
the weighing device exhibits an electrical value indicator, wherein the electrical value indicator emits an electrical control signal, corresponding to changing weight of the second flexible container (5'), to the electromotor, wherein the electromotor is attached to the clamping block (7) and acts on the displacement device for a controlled back-and-forth shifting of the wedge (12) within the cross channel (11) of the clamping block (7).

20. The device according to claim 8, wherein
a mechanical eccentric cam (23) for an opening is disposed coordinated to the breaker unit (8) as a clamping unit for the light-transparent connection (6), wherein upon actuation the mechanical eccentric cam (23) for the opening opens a flow cross-section of the light-transparent connection (6) very slowly relative to a speed of flow of the blood constituents.

21. The device according to claim 20, wherein
the clamping unit is integrated into the breaker unit (8), and wherein a movable part of an electromagnet (16) is capable of opening very slowly relative to the speed of flow of the blood constituents.

22. The device according to claim 21, wherein
the clamping unit is integrated into a flow-limiting unit (7), and wherein a wedge (12) is movable additionally as an eccentric cam for the opening with an electromotor (22).

* * * * *